United States Patent [19]

Wagner et al.

[11] Patent Number: 4,927,920

[45] Date of Patent: May 22, 1990

[54] SUGAR ESTER SYNTHESIS

[75] Inventors: Frederick W. Wagner, Walton; Rebecca S. de la Motte; Maria A. Dean, both of Lincoln, all of Nebr.

[73] Assignee: Nebraska Department of Economic Development, State of Nebraska, U.S.A., Lincoln, Nebr.

[21] Appl. No.: 271,661

[22] Filed: Nov. 15, 1988

[51] Int. Cl.$^5$ .................... C07H 13/02; C07H 11/00; C07H 1/00; C07H 1/06

[52] U.S. Cl. .................................. 536/119; 536/115; 536/124; 536/127

[58] Field of Search ................. 536/119, 115, 124, 127

[56] References Cited

U.S. PATENT DOCUMENTS

| | | | |
|---|---|---|---|
| 2,893,990 | 7/1959 | Hass et al. | 536/119 |
| 3,644,333 | 2/1972 | Osipow et al. | 536/119 |
| 3,748,324 | 7/1973 | Mizutani et al. | 536/119 |
| 4,611,055 | 9/1986 | Yamamoto et al. | 536/119 |
| 4,614,718 | 9/1986 | Seino et al. | 435/72 |
| 4,683,299 | 7/1987 | Kea et al. | 536/119 |
| 4,710,567 | 12/1987 | Kea et al. | 536/119 |

Primary Examiner—Ronald W. Griffin
Assistant Examiner—Everett White
Attorney, Agent, or Firm—Lucas & Just

[57] ABSTRACT

This method for making sugar esters entails first reacting a sugar and an ester of that sugar having a degree of substitution greater than 2 with a Lewis acid or Lewis base catalyst in an organic solvent to form a sugar ester having a degree of substitution up to 2 and recovering the sugar ester having a degree of substitution up to 2 at ambient temperature. The recovery step must be conducted at a temperature below the distillation or boiling temperature of the organic solvent or else the DS of the resulting sugar ester will be greater than 2. This process is especially suited for sucrose esters. The reaction between the sugar and the sugar ester is conducted in the absence of a methyl ester of a fatty acid.

11 Claims, No Drawings

SUGAR ESTER SYNTHESIS

This invention relates to sugar esters and, more specifically, to a method of making sugar esters by reacting a sugar with an ester of that sugar having a degree of substitution (DS) greater than 2 and recovering the resulting sugar ester having a DS up to about 2.

The properties, synthesis and purification of fatty acyl esters of sugar (hereafter referred to as sugar esters) have been under investigation since the early 1950's. The excellent behavior of these materials as surfactants and nonionic emulsifiers, as well as their ready biodegradation into naturally occurring nutrient substances, have made them the additive of choice in several food-processing and cosmetics applications.

There exist several U.S. patents relating to the technology of sucrose ester synthesis and purification. Patents concerned with the synthesis may be roughly classified into four categories: those in which a transesterification from fatty acyl methyl esters to sucrose is base-catalyzed in anhydrous solvents (e.g. U.S. Pat. No. No. 2,893,990); those in which a transesterification is base-catalyzed from a fatty acyl methyl ester in a microemulsion under conditions that remove the product, methanol, by vacuum distillation ("transparent emulsion" technology, e.g. U.S. Pat. No. 3,644,333); those in which fatty acyl chlorides are used as acyl donors in anhydrous solvents (e.g. U.S. Pat. No. 4,683,299); and those in which an esterification or transesterification is enzyme-catalyzed in either aqueous or nonaqueous solution (e.g. U.S. Pat. No. 4,614,718).

Of these various methods, those which have been best adapted to the industrial-scale production of food-grade sucrose esters are the transparent emulsion techniques. These processes have displaced earlier technologies because they allow circumvention of the difficult problem of finding a solvent system which is acceptable in food additive manufacture, and which also has the ability to solublize both the very hydrophilic sugar component and the very hydrophobic acyl donor.

U.S. Pat. No. 3,644,333 describes a water-based transparent emulsion process which has found use in the industrial-scale manufacture of sugar esters. In this method, a microemulsion of methyl tallowate in aqueous sucrose solution is prepared by the inclusion of suitable emulsifiers into the reaction mixture. The water is removed by vacuum distillation and solid potassium carbonate is added as a catalyst. The product is obtained in crude form as a waxy dark brown cake after a period of heating in the presence of the catalyst. This material contains from 10% to 80% nascent sucrose esters, with the balance consisting of unreacted sucrose, the initially added emulsifiers and reaction by-products.

Removal of contaminating materials from the crude reaction product is not difficult, since the solubility properties of the contaminants are very different from those of the sucrose esters (for example, see U.S. Pat. No. 3,748,324). However, the sucrose ester fraction obtained from such a purification is not, in general, homogeneous with respect to degree of acylation; rather, it is a complex mixture of esters resulting from arbitrary acylation of the sugar hydroxyl groups. Among these various esters, the most valuable products are those exhibiting a degree of substitution of one or two, since the high hydrophile-lipophile balance (HLB) of these materials is such as to make them useful emulsifying agents. Thus, in order for the sugar ester reaction product to constitute a useful emulsifier, the esters must be fractionated according to degree of acylation. In particular, the less substituted esters must be obtained in a preparation which is relatively free of higher esters.

Purification procedures directed toward resolving sucrose esters according to degree of acylation are lengthy and complex, (e.g. U.S. Pat. No. 4,710,567) because the emulsifying nature of the material complicates phase partitioning in solvent extractions. The cost associated with this fractionation makes the final product too expensive for use as a bulk emulsifier in some applications, even when the emulsifying properties of the sucrose ester product are superior to those of less expensive conventional emulsifiers such as mono- and diglycerides.

Moreover, the necessity of fractionating the ester product from transparent emulsion processes cannot be overcome by manipulating the molar ratio of sugar to acyl donor in the reaction mixture. This is due to the fact that the formation of the microemulsion required for an efficient reaction is a delicate function of the proportions of reactants and accessory emulsifiers.

U.S. Pat. No. 2,893,990 teaches a transesterification process involving distillation in the recovery of the product. Such a process produces sugar esters typically having a DS greater than 2 and is unable to produce predominately sugar esters having a DS up to about 2.

It has now been discovered that the step of fractionation can be avoided by employing the method of the present invention. It has also been discovered that the method of the present invention provides mainly monosubstituted sugar esters and to a lesser degree diesters.

Broadly, the process of the present invention comprises the steps of reacting a sugar with an ester of that sugar having a degree of substitution greater than 2 in an organic solvent at a temperature below the decomposition temperature of both the sugar and the ester of that sugar in the presence of a catalyst to form a resulting sugar ester having a degree of substitution up to about 2, removing the catalyst from the solvent and recovering the resulting sugar ester. If the catalyst is not removed from the solvent prior to recovering the resulting sugar ester for the solvent, then the resulting sugar ester must be recovered by means that employ a temperature below the distillation temperature of the organic solvent. It has been found that by employing a high temperature in the presence of the catalyst causes the predominately mono sugar ester to convert to poly sugar ester.

One of the unique features of the present invention is that methyl esters of fatty acids are not required. The reaction between the sugar and an ester of that sugar having a degree of substitution greater than 2 in the absence of a methyl ester of a fatty acid.

The process of the present invention replaces the complicated fractionation step and allows for production of mono- and disubstituted sugar esters. Degree of substitution (DS) as used in the specification and claims means the number of acyl groups that are chemically bonded to a sugar molecule. For example, if a sucrose ester has two acyl groups attached to the sucrose molecule, it has a DS of 2.

Suitable sources of sugar esters having a DS greater than about 2 are a crude product from a de novo synthetic process; the ester product from such a synthesis after removal of residual reactants, ancillary additives and by-products; or commercially available purified sugar esters with components exhibiting more than two acyl substituents.

Suitable organic solvents include dimethyl sulfoxide, dimethyl formamide, acetonitrile, acetone, acetic acid, 1,2-dimethoxyethane, 2-methoxyethyl ether, or any alcohol which does not behave as a nucleophile in the transesterification (such as 2-propanol).

The catalyst used is either a Lewis acid or Lewis base. Suitable Lewis base catalysts are alkali carbonate, hydroxide, or alkoxide, or an organic amine. Suitable Lewis acid catalysts are mineral acids such as hydrochloric or sulfuric acid, or an organic acid such as acetic acid. Good results have been obtained using an alkali metal carbonate. The amount of Lewis catalysts used is preferably about 0.001 to about 0.1 by weight of sucrose.

The reaction is performed at any temperature below that at which the reactants, i.e. sugar and an ester of that sugar having a DS greater than 2, decompose in the chosen solvent. Preferably, the temperature ranges between about 20° C. to about 160° C. and, more preferably, from about 60° C. to about 120° C. For sucrose esters, the best results have been obtained employing a temperature in the range of about 90° C. to about 100° C. Pressure can be employed so that the boiling point of the desired solvent is increased. The time of the reaction will vary with conditions. The reaction time required is usually between 30 minutes to 48 hours. With sucrose esters, the preferred reaction time is about 20 to about 30 hours.

Suitable sugars include monosaccharides such as glucose, fructose, ribose, arabinose, mannose, xylose or galactose; disaccharides such as maltose, cellobiose, lactose, or trehalose; trisaccharides such as maltotriose, raffinose, cellotriose or manninotriose; tetrasaccharides such as cellotetrose or stachyose; or polysaccharides such as dextrin, cyclodextrin, dextran, mannan, fructan, galactan, xylan, araban, or cellulose. The preferred sugar is sucrose.

The sugar reactant and the sugar molecule of the sugar ester reactant should be the same sugar in order to obtain a single pure sugar ester having a DS of up to about 2.

The ratio of sugar to sugar ester having a DS greater than 2 depends on the DS of the ester. Preferably, enough sugar is added to stoichiometrically provide a resulting sugar ester having a DS up to 2.

If the catalyst has not been removed from the reaction vessel, it is critical that the step of recovering the resulting sugar ester from the organic solvent be conducted at a temperature below the distillation temperature of the organic solvent and preferably between about 25° C. to about 40° C. Best results are obtained at ambient temperature. If high temperatures are used, transesterification occurs between the sugar molecules and the DS of the resulting sugar esters will typically be greater than 2. Applicants have found that the temperature must be below the distillation temperature of the organic solvent. Methods for recovery of the resulting sugar esters from solution include partition chromatography.

If the catalyst is removed from the reaction vessel, then the resulting sugar esters can be obtained by removing the solvent by distillation. Suitable means for removing the catalyst from the organic solvent include partitioning or partition chromatography. Where the catalyst is alkali metal carbonate, the carbonate is preferably decomposed to carbon dioxide and the carbon dioxide removed by vacuum. Alternatively, the sugar ester product and organic solvent is separated from the catalyst and the sugar ester product is subsequently recovered from the organic solvent.

These and other aspects of the present invention will be more fully understood by reference to the following examples.

EXAMPLE 1

One gram of commercially prepared crude sucrose esters from a transparent emulsion process having a DS greater than 2 was crushed and thoroughly mixed with 1 gram of anhydrous sucrose. The dry reagents were added to 25 mls of anhydrous dimethylformamide, with 0.1 gram potassium carbonate added as catalyst. The closed reaction vessel was heated to 90° C. with stirring. After 8 to 30 hours, the reaction vessel was cooled and an aliquot of the reaction was removed for thin layer chromatography (TLC) analysis. The remainder of the reaction solution was used for bulk recovery of sugar esters.

The reaction mixture aliquot was extracted with an equal volume of ethanol-chloroform (1:1), and spotted on silica plates developed in hexane:ethanol:ether:acetic acid (60:20:20:1). Plates were sprayed with a 10% phosphoric acid, and 5% cupric acetate, and charred at 190° C. to visualize organic compounds. This method allowed visualization of the extent of reaction and approximation of yield by comparison with standard solutions. TLC of the crude esters showed a range of substituted esters, with the spots of lower Rf corresponding to the less substituted sucrose esters, and the spots of higher Rf corresponding to higher substituted sucrose esters. Comparison of the TLC results of the reaction aliquot with that of the crude esters showed almost complete conversion of higher substituted crude esters to the sucrose esters having a DS up to 2, with little increase in the amount of free fatty acid released in the reaction.

For bulk recovery of the sucrose esters, the cooled reaction solution was applied to a silica gel column and was eluted with hexane:ethanol:ether (60:20:20). Purified sucrose mono- and diesters were recovered, 300–600 mgs, with the amount recovered dependent on the crude ester source.

EXAMPLE 2

Ten grams of highly esterified sucrose esters, having a DS greater than 2, (such as HLB-1, previously purified from a crude ester preparation), 10 grams of anhydrous sucrose and 1 gram of anhydrous potassium carbonate were added to 250 mls of anhydrous dimethyl formamide. The reaction vessel was heated to 90° C. with constant stirring. After 28 hours, the reaction vessel was cooled and the solution was decanted. TLC, bulk recovery and Fast Atom Bombardment (FAB) Mass Spectrometry were performed. Seven grams of sucrose mono and diesters were recovered. TLC results comparing the untreated sucrose esters (HLB-1) and the reaction products were dramatic in that the untreated samples had spots primarily with high Rf values whereas the sample from the reaction mixture exhibited spots of entirely low Rf values.

FAB Mass Spectrometry was used to determine the amount of fatty acid substitution on the sucrose ester. Typical sucrose ester samples from the examples listed contain 80% monoester and 20% diester, while commercially purified samples of low esterified sucrose esters (such as HLB-15) appeared to contain 30% monoester and 70% diester, when analyzed under identical conditions.

Two grams of highly esterified sucrose esters, having a DS greater than 2, (such as HLB-1), 3 grams of anhydrous sucrose and 0.5 gram of anhydrous potassium carbonate were added to 80 mls of anhydrous acetone and placed in a sealed reaction vessel. The reaction vessel was heated with stirring to a constant temperature of 103° C. for 48 hours. After cooling, the acetone was removed by heating (40° C.) of the open reaction vessel. The resulting solid was extracted several times with small volumes of 2-butanone to selectively solvate the sucrose esters. Evaporation of the solvent yielded 1.2 grams of solid, which was shown by TLC to consist primarily of sucrose mono- and diesters.

EXAMPLE 4

The reactants and conditions of Example 2 were used for a reaction time course study of the transesterification reaction. The conversion of highly esterified sucrose esters to mono-.and disubstituted sucrose esters was monitored via TLC analysis, from aliquots of the reaction removed at regular time intervals. After six hours, the TLC analysis showed approximately half conversion of the highly esterified esters to the lower esterified sucrose esters. After 11 hours, approximately eighty percent (80%) conversion had occurred; after 8 to 24 hours, the conversion was nearly complete with little change in later TLC aliquots.

EXAMPLE 5

In this example, triethylamine (0.025 mls) was used as the Lewis base catalyst and was added to 0.01 gram of highly esterified sucrose esters (HLB-1), 0.01 gram anhydrous sucrose, and 0.4 mls of anhydrous dimethylformamide. The reaction vessel was sealed and heated to 103° C. After 48 hours, a 50% conversion of highly esterified esters to low esterified esters was estimated from TLC analysis and comparison with standard solutions under the same conditions.

EXAMPLE 6

In this example, anhydrous acetonitrile (0.4 mls) was used as the reaction solvent and was added to 0.01 gram of highly esterified sucrose esters (such as HLB-1), 0.01 gram anhydrous sucrose, and 6 mgs of potassium carbonate. The reaction vessel was sealed and heated to 103° C. After 86 hours, a 70% conversion of highly esterified esters to low esterified sucrose esters was estimated from TLC analysis and comparison with standard solutions under the same conditions.

EXAMPLE 7

Triethylamine (0.05 mls) was used as the catalyst and was added to 0.25 gram of highly esterified sucrose esters (such as those obtained from the purification of sucrose polyesters from the melt process of U.S. Pat. No. 3,792,041), 0.25 gram anhydrous sucrose and 5.0 mls of dimethylsulfoxide in a sealed reaction vessel. The reaction vessel was heated at 90° C. with stirring of the reaction solution. TLC analysis showed an 80% conversion of highly esterified esters to low esterified esters after 30 hours.

EXAMPLE 8

Tetramethylurea (1.5 mls), as the reaction solvent, was added to 0.2 gram sucrose, 0.01 gram potassium carbonate and 0.1 gram of highly esterified sucrose esters (such as HLB-1). The reaction vessel was heated with stirring to a temperature of 90° C. After 24 hours, TLC analysis showed only mono- and diesters of sucrose in the reaction solution. Triethylamine (0.05 mls) can be substituted for potassium carbonate as the base catalyst.

EXAMPLE 9

Ten grams of a crude ester preparation (as prepared by the melt procedure in U.S. Pat. No. 3,792,041) was found to contain 25% sucrose mono- and diester of the total sucrose ester content. The unpurified crude ester preparation was added to 25 mls of dimethylformamide, 5 grams of sucrose, and 0.9 gram potassium carbonate and was stirred and heated at 90° C. for 24 hours. The monoester content of the preparation increased to 95% of the total sucrose ester content as seen by FAB Mass Spectrometry and TLC analysis.

EXAMPLE 10

Example 2 is repeated except, after cooling the reaction vessel, the remaining potassium carbonate is allowed to settle to the bottom of the vessel and the organic solvent and resulting products were decanted off. Then the organic solvent was distilled, leaving the sucrose ester having a DS less than 2.

Certain sugar derivatives and their esters exhibit unique, desirable properties as ionic or nonionic emulsifiers and may be used as the sugar base in the reaction. Sugar derivatives applicable in this invention may include sugar alcohols, such as sorbital, sorbitan, mannitol, xylitol, arabitol or dulcitol; sugar amines such as glucosamine; and oxidation products or sugars such as gluconolactones or gluconic acid.

It will be understood that the claims are intended to cover all changes and modifications of the preferred embodiments of the invention which have been chosen herein for the purpose of illustration and do not constitute a departure from the spirit and scope of the invention.

What is claimed is:
1. A process of making a sugar ester having a DS up to 2, comprising the steps of:
   (a) reacting only a sugar and an ester of said sugar having a DS greater than about 2 in an organic solvent in the presence of a transesterification catalyst to form a sugar ester having a DS up to 2; and
   (b) recovering said sugar ester having a DS up to 2 at a temperature below the boiling point of said organic solvent.
2. The process of claim 1 wherein the reaction between the sugar and the ester of said sugar is conducted in the absence of a methyl ester of a fatty acid.
3. The process of claim 2 wherein the temperature in step (b) is ambient.
4. The process of claim 2 wherein the sugar is sucrose.
5. The process of claim 2 wherein the transesterification catalyst is a Lewis acid or Lewis base.
6. The process of claim 3 wherein the sugar is sucrose.
7. A process of making a sugar ester having a DS up to 2, comprising the steps of:
   (a) reacting only a sugar and an ester of said sugar having a DS greater than about 2 in an organic solvent in the presence of a transesterification catalyst to form a sugar ester having a DS up to 2;

(b) separating said catalyst from said sugar ester having a DS up to 2; and
(c) recovering said sugar ester having a DS up to 2 from said organic solvent.

8. The process of claim 7 wherein the reaction between the sugar and the ester of said sugar is conducted in the absence of a methyl ester of a fatty acid.

9. The process of claim 7 wherein the sugar ester is recovered from the organic solvent by distillation.

10. The process of claim 7 wherein the sugar is sucrose.

11. A process of making a sugar ester having a DS up to 2, comprising the steps of:
(a) reacting only a sugar and an ester of said sugar having a DS greater than about 2 in an organic solvent in the presence of an alkali metal carbonate transesterification catalyst and the absence of a methyl ester of a fatty acid to form a sugar ester having a DS up to 2;
(b) separating the transesterification catalyst from said sugar ester having a DS up to 2; and
(c) recovering said sugar ester having a DS up to 2 from said organic solvent.

* * * * *